(12) United States Patent
Manoussakis et al.

(10) Patent No.: US 7,500,569 B2
(45) Date of Patent: Mar. 10, 2009

(54) PLASMA ON DEMAND TUBE

(75) Inventors: Dimitrios Manoussakis, Wyckoff, NJ (US); Robert J. Losada, Astoria, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 587 days.

(21) Appl. No.: 11/015,949

(22) Filed: Dec. 17, 2004

(65) Prior Publication Data

US 2005/0139547 A1 Jun. 30, 2005

Related U.S. Application Data

(60) Provisional application No. 60/532,509, filed on Dec. 24, 2003.

(51) Int. Cl.
*B01L 3/14* (2006.01)
*B65D 39/00* (2006.01)

(52) U.S. Cl. .................. 210/406; 210/472; 422/101; 422/102

(58) Field of Classification Search ............... 436/177; 600/576, 577; 422/73, 101, 102; 604/6.04, 604/6.07, 6.09; 210/406, 472
See application file for complete search history.

(56) References Cited

U.S. PATENT DOCUMENTS

| 3,492,396 A | 1/1970 | Dalton et al. |
| 3,902,964 A | 9/1975 | Greenspan |
| 4,424,279 A * | 1/1984 | Bohn et al. .................. 436/534 |
| 4,753,776 A * | 6/1988 | Hillman et al. .............. 422/101 |
| 4,933,092 A * | 6/1990 | Aunet et al. ................. 210/729 |
| 5,275,731 A | 1/1994 | Jahn |
| 5,364,533 A * | 11/1994 | Ogura et al. ................. 210/645 |
| 5,981,294 A | 11/1999 | Blatt et al. |
| 6,465,202 B1 * | 10/2002 | Tyrrell .......................... 435/15 |
| 6,506,167 B1 | 1/2003 | Ishimito et al. |
| 6,659,288 B2 * | 12/2003 | Amano et al. ................ 210/406 |
| 2003/0013205 A1 | 1/2003 | Konrad |

FOREIGN PATENT DOCUMENTS

| EP | 1477804 A1 | 11/2004 |
| WO | WO0229406 A1 * | 4/2002 |

* cited by examiner

*Primary Examiner*—Terry K Cecil
(74) *Attorney, Agent, or Firm*—Mark Lindsey

(57) ABSTRACT

A device for separating plasma from whole blood is provided having an evacuated primary collection chamber capable of fluid communication through a porous filter to an evacuated secondary collection chamber. An agglutinating agent is provided within the primary collection chamber so as to aggregate blood cells within a whole blood sample. The porous filter has a pore size which is small enough to capture the aggregated blood cells therein, yet large enough to permit plasma to transfer therethrough under pressures associated with conventional evacuated blood collection tubes. The primary and secondary collection chambers may be provided in separate containers or tubes, with transfer occurring therebetween through a transfer device including the porous filter therein.

8 Claims, 13 Drawing Sheets

PLASMA ON DEMAND TUBE

CROSS-REFERENCE TO RELATED APPLICATION

This application claims the benefit of U.S. Provisional Application No. 60/532,509, filed Dec. 24, 2003.

BACKGROUND OF THE INVENTION

1. Field of the Invention

The present invention relates to separation of plasma from whole blood. Particularly, the present invention relates to a medical device capable of separating plasma from agglutinated blood cells through a porous filter membrane.

2. Description of Related Art

Plasma is the liquid portion of blood primarily comprised of water. The water portion of the plasma is freely transferable with cells of the body and other extra cellular fluids. Plasma is also comprised of salts, glucose, amino acids, vitamins, hormones and metabolic waste products. As a whole, plasma provides the means to suspend white blood cells, red blood cells and other cellular components for transfer through a human or animal. If a plasma sample is desired, separation from the other cellular components of blood must occur well before coagulation of the blood. Once the blood coagulates, serum is the remaining liquid portion of the collected blood sample, which is devoid of some protein components of blood.

Because plasma contains a rich source of components available for diagnostic analysis, medical devices are available for use in separating plasma from a whole blood sample. Several prior art examples provide evacuated multi-chamber devices, which incorporate a filter used to yield plasma removed from a collected blood sample. In some of the prior art examples, the devices use a detachable chamber, allowing a user to access the separated plasma specimen. In addition, the prior art devices typically use a filter membrane having small and fine pore sizes to prevent cellular components from passing therethrough, which can render the vacuum forces generated by the evacuated device inadequate to drawn plasma from a collected blood sample.

Ishimito et al. disclose a blood separating tube in U.S. Pat. No. 6,506,167 entitled, "Blood-Collecting Tubes," including an upstream tube separated by a filter from a downstream tube where the tubes are attachable to and detachable from each other and are evacuated. During blood collection, blood is removed from a patient through intravenous puncture and transferred into the upstream tube through blood pressure and negative pressure inside the tube. In accord with the disclosure, a pressure differential is supposed to be created between the upstream tube and the downstream tube as the blood contacts the filter between the two tubes. Several suggested filters include a membrane, glass fibers, filter paper with large pores having attached thereto anti-hemocyte antibodies, a filter impregnated with a cationic macromolecular substance to aggregate cells, and a laminated multi-layer filter. Problems that exist with this disclosure are blood cells clogging the filter and an inadequate vacuum force between the upstream tube and downstream tube during blood collection. A further problem that exists with this disclosure is exposing any plasma collected in the downstream tube to contaminants should the downstream tube be removed from the upstream tube.

Konrad, in United States Patent Application Publication No. 2003/0013205, entitled "Separating Device," describes a preferred method of producing a concentration of nucleic acids, RNA or DNA, from whole blood by way of a liquid-permeable separating element. The separating elements disclosed include filters, silicate membranes, ion-exchange membranes and columns or separating columns. It is disclosed that the invention is capable of causing the release of nucleic acid molecules from the cellular components of the blood through lysis. The collected sample containing lysed blood cells is passed through a separating element, which is capable of adsorbing the nucleic acid component. The separating element can be removed for later molecular diagnostic analysis. Konrad does not disclose plasma separation from whole blood.

Murto et al., in World Intellectual Property Organization International Publication No. WO 02/29406 entitled "Methods and Devices for Processing Blood Samples," describes methods and related devices and reagents for separating plasma from a whole blood sample. The invention as disclosed describes a method of separating plasma from the cellular components of whole blood by mixing a reagent comprising magnetically attractable particles having an agglutinating agent bound thereto with a whole blood sample. The purpose of the magnetic reagent is to bind the cellular components of the whole blood sample. A magnetic force is then applied to the mixture to separate the magnetic reagent with cells bound thereto from the plasma. The plasma is separated from the mixture by pipetting, decanting, siphoning or wicking.

There is a present need for a device that is capable of providing sufficient force by the internal vacuum force of the tubes to separate agglutinated blood cells from plasma without clogging of the filter, and which is easy to use in clinical and research applications while providing an uncontaminated plasma specimen.

SUMMARY OF THE INVENTION

Generally, the present invention is directed to a device for separating plasma from whole blood, including a primary collection chamber having a blood agglutinating agent and an anticoagulant deposited therein, and a porous filter separating the primary collection chamber from a secondary collection chamber. A transfer device having at least one needle may be provided to transfer plasma from the primary collection chamber to the secondary collection chamber. The invention is an improvement over the prior art as it is capable of providing sufficient force by the vacuum in the evacuated tubes to separate plasma from agglutinated, but uncoagulated, blood cells with a large pore filter that is less prone to clogging with aggregated blood cells. The use of an agglutinating agent to aggregate the cells, in combination with a filter having a larger pore size, permits separation of plasma from the aggregated cells with the use of conventional evacuated tubes, which, because of this combination, have adequate vacuum to draw the plasma through the filter. The invention is a further improvement over the prior art as it is easy to use in clinical and research applications. The invention is an even further improvement over the prior art as it is capable of providing an uncontaminated plasma specimen that is separated from a whole blood sample.

In one aspect of the invention, an agglutinating agent alone is used, which causes the cells present in the sample to aggregate together. In this embodiment, the cells themselves can be considered the "starting particles" to which additional cells will stick or aggregate.

In an additional aspect of the invention, a structure coated with an agglutinating agent can be used, and the coated structures are the starting particles, to which the cells stick or aggregate.

In one embodiment of the present invention, the primary collection chamber is provided in an evacuated collection tube hermetically sealed with a pierceable rubber stopper. A vent needle, which is gas permeable, is optionally provided that may be inserted through the pierceable rubber stopper. An agglutinating agent is present within the primary collection chamber to aggregate blood cells in a whole blood sample that is collected within the primary collection chamber. Moreover, an anticoagulant may coat the surface of the internal wall of the primary collection chamber to prevent coagulation of the whole blood sample collected within the primary collection chamber.

A transfer device is further provided in the form of a cylinder with a hollow partition internally attached within the device. The interior walls of the cylinder and the partition define an upstream chamber and a downstream chamber. A porous filter, which is capable of separating plasma from aggregated blood cells, is held within the hollow partition. Two needles are mounted in the partition surface, whereby the needles are positioned on opposing sides of the filter. The two needles provide fluid communication into and out of the hollow partition through the filter. As such, blood can enter the hollow partition at the upstream end of the transfer device, with plasma passing through the porous filter, through the downstream end and out of the transfer device into a secondary chamber. The secondary chamber is desirably a secondary tube having an evacuated collection tube hermetically sealed with a pierceable rubber stopper.

In a further embodiment, the primary collection chamber is provided as an evacuated, double-ended collection tube hermetically sealed at both ends with pierceable rubber stoppers. A cylindrical porous filter is secured within the primary collection chamber whereby the porous filter lies adjacent to and abuts against an annular shoulder of a pierceable rubber stopper. A vent needle, which is gas permeable, is optionally provided that may be inserted through the pierceable rubber stopper sealed at the upstream end of the primary collection chamber.

In yet a further embodiment, the primary collection chamber is provided in an evacuated collection tube that is hermetically sealed with a pierceable rubber stopper. A cylindrical porous filter having a central bore through the length of the filter is secured within the primary collection chamber at a location adjacent the pierceable rubber stopper end of the collection tube. A rubber one-way valve is attached to the porous filter at one end of the central bore, thereby sealing the bore. The one-way valve allows whole blood being collected to flow into the primary collection chamber. A vent needle, which is gas permeable, is optionally provided that may be inserted through the pierceable rubber stopper.

An alternate transfer device is provided for use with such embodiments of the collection tube, which includes a cylinder including an internal solid partition attached therein. The partition separates the cylinder into an upstream chamber and a downstream chamber, defined within the interior walls of the cylinder. A double-ended needle is mounted through the partition, whereby the needle extends perpendicular to the surfaces of the partition, and provides fluid communication through the partition of the transfer device between the upstream and downstream chambers. As such, a primary collection tube as described above can be inserted into the upstream chamber with the upstream end of the needle piercing the stopper of the primary collection tube. A secondary chamber, such as a secondary evacuated tube sealed with a rubber stopper, can then be inserted within the downstream chamber and pierced by the downstream end of the needle, with plasma flowing through the filter and through the transfer device, into the secondary chamber of the secondary evacuated tube.

In an alternate embodiment, a double-ended collection tube that is hermetically sealed at both ends with pierceable rubber stoppers is provided. A cylindrical porous filter is secured between the two ends of the tube, desirably at a location that is equidistant from each end of the double-ended collection tube. The porous filter provides a separation defining a primary collection container and a secondary chamber within the single tube. An agglutinating agent and an anticoagulant are present within the primary chamber of the tube. As such, blood collected within the primary chamber is contacted with these agents, causing the cells to aggregate. Negative pressure within the secondary chamber can then draw the plasma through the filter into the secondary chamber, where it can thereafter be further transferred to a separate container, such as through a separate transfer device attached with an additional collection tube piercing the stopper at the secondary chamber downstream end of the tube. A vent needle, which is gas permeable, is optionally provided that may be inserted through the pierceable rubber stopper at the upstream end of the tube to access the primary collection chamber during use.

DETAILED DESCRIPTION OF THE INVENTION

Figure 1:
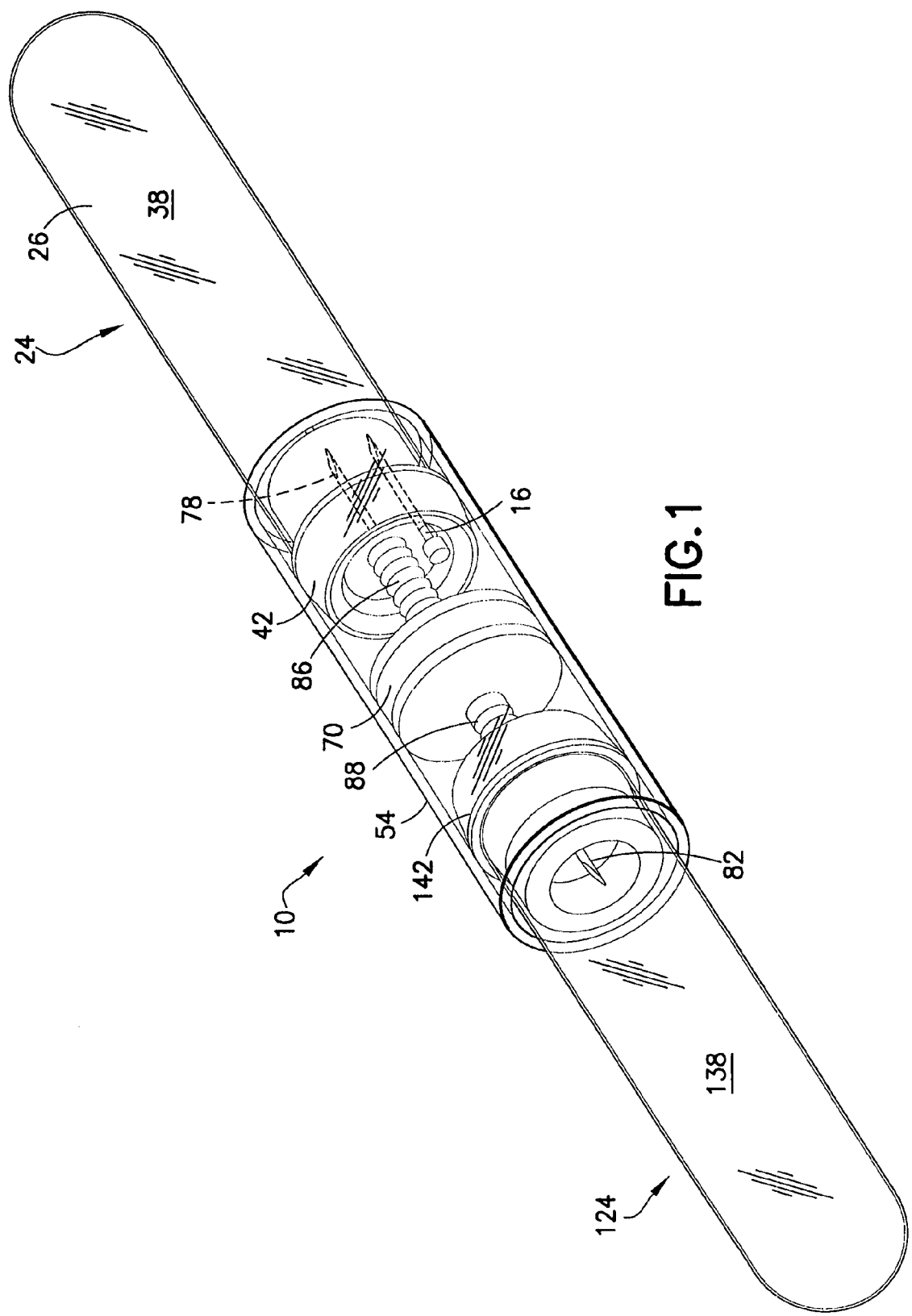
FIG. 1 is a perspective view of a preferred embodiment of a device having evacuated primary and secondary tubes with a transfer device having a filter disposed therein made in accord with the present invention.
Figure 2:
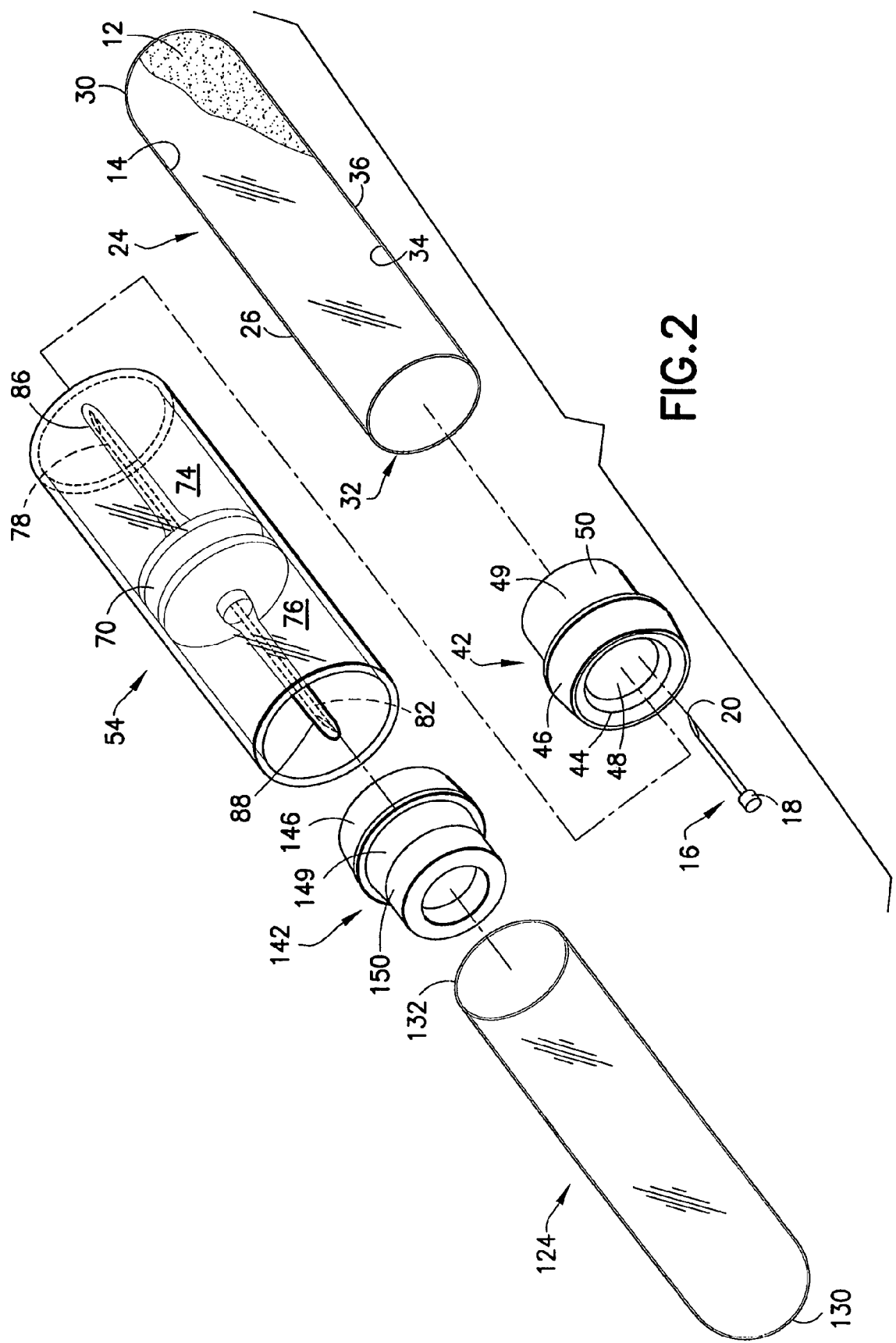
FIG. 2 is an exploded view of the device as shown in FIG. 1.
Figure 3:
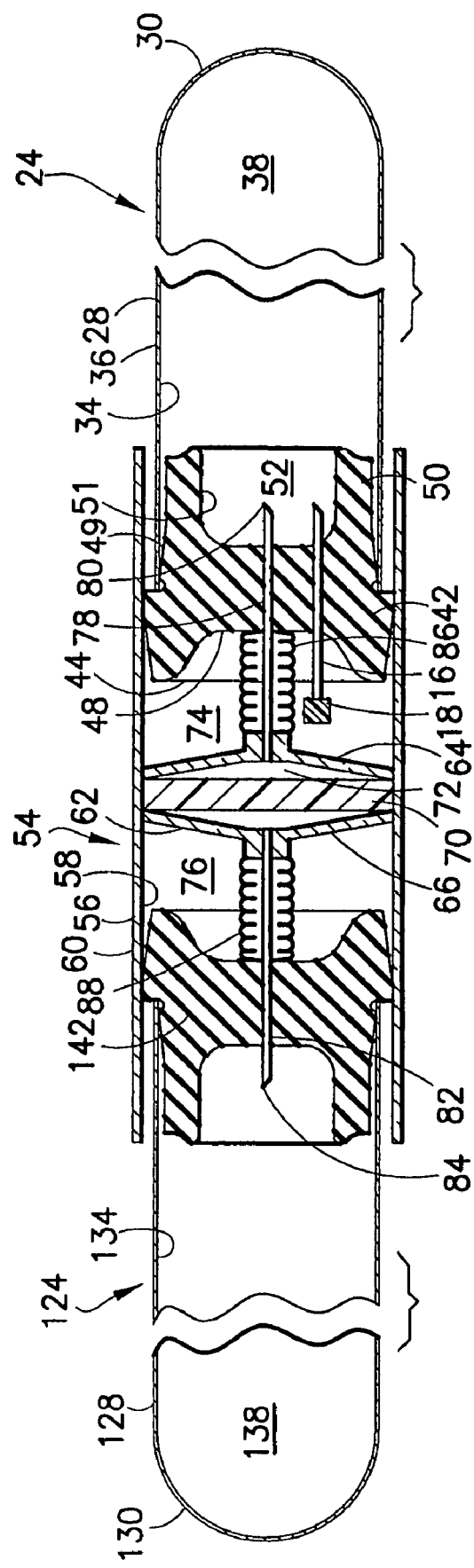
FIG. 3 is a sectional view of the device as shown in FIG. 1.

Referring to the drawings in which like figures refer to like parts throughout the several views thereof, FIGS. 1-3 illustrate an assembly for separating plasma from whole blood. The present invention is generally described in terms of a blood collection and plasma separation device 10, which is defined generally by primary tube 24 enclosing primary collection chamber 38, secondary tube 124 enclosing secondary collection chamber 138, and transfer device 54 housing porous filter 72.

The purpose of the present invention is to separate plasma from the cellular components of blood by exposing blood in a primary collection chamber such as a primary tube to an agglutinating agent to create large aggregates of blood cells. Then, a pressure differential is used to draw the mixture of aggregate blood cells and plasma into a porous filter, whereby the aggregate blood cells become trapped and a difference in pressure between the primary collection chamber and a secondary collection chamber, such as a secondary tube, continues to draw the plasma through the porous filter into the secondary collection chamber. The primary tube can be used with any medical device capable of either collecting blood directly from a patient or indirectly from a previously collected blood sample, such as any blood collection device that includes a piercing element or allows for attachment to a catheter.

Some terms are used universally throughout the specification. The terms "upstream" and "downstream" are used in reference to the assembly of the invention while in use, which is when the primary tube and secondary tube are connected to the transfer device during plasma transfer. Structurally, the terms upstream and downstream are relative terms used in reference to plasma flow from upstream in the primary collection chamber to downstream in the secondary collection chamber during use. The term "anticoagulant" is used to describe any compound known in the art, such as heparin, capable of preventing blood coagulation.

As shown in detail in FIGS. 1-3, primary tube 24 comprises tube 26 hermetically sealed with rubber stopper 42. Tube 26 includes generally cylindrical tubular wall 28 extending between closed end 30 and open end 32. Tube 26 has interior surface 34 and exterior surface 36. Tube 26 is comprised of a suitable material, which is impermeable to gas and liquid, and is desirably made of glass or molded plastic.

Rubber stopper 42 is an elastomeric closure which is comprised of a suitable material capable of providing open end 32 of tube 26 with a gas- and liquid-tight seal, and capable of being punctured or pierced with an appropriate medical device, such as a needle, for transfer of blood into tube 26. Rubber stopper 42 includes a main portion 46 centrally molded with depending portion 50. Depending portion 50 extends from main portion 46, with depending portion 50 capable of extending into open end 32 of tube 26. Depending portion 50 may be annular, having cavity 52. Rubber stopper 42 may include top surface 44 with depending recess 48 centrally molded or fabricated thereon.

The space within interior surface 34 of tube 26 and interior surface 51 of cavity 52 of depending portion 50 of rubber stopper 42 define primary collection chamber 38 of tube 26. Tube 26 is an evacuated tube, in that the interior space within tube 26, which defines primary collection chamber 38, has a negative pressure or a reduced pressure relative to the respective ambient pressure, such as compared with blood pressure or with atmospheric pressure. In this manner, a type of vacuum can be established within tube 26 to draw fluid therein from an external environment, as is well known in the art.

Prior to evacuating tube 26 and hermetically sealing circumferential surface 49 of depending portion 50 of rubber stopper 42 to interior surface 34 of tube 26, interior surface 34 of tube 26 may be coated with anticoagulant 14. An agglutinating agent 12 is then deposited inside tube 26. Such agglutinating agent 12 may be any compound that is capable of binding blood cells suspended in whole blood to create large aggregates of blood cells. Examples of specific agglutinating agents include lectins, such as potato or wheat lectins. Alternative agglutinating agents may include antibodies with an affinity for blood cells attached to microbeads. The agglutinating agent may be in the form of a solution, pellet, pill, or lyophilized specimen, such as granules. The term "agglutinating agent" is used to denote the use of an agglutinating agent alone to form cell aggregates, or the use of an agglutinating agent in combination with a structure that can impart desired properties to the cellular aggregates. In this embodiment, the structure can be specially designed to have specific desired properties. For example, the structure can be a microbead of a particular density, coated with an agglutinating agent. If it is desired to have the aggregated cells float on top of the sample, a bead having a lower density than that of plasma can be used, such that when aggregated on the beads, the aggregated cells float on top of the sample, thereby preventing clogging of the filter and permitting the plasma to pass. In another non-limiting example, the structure can have a specific geometry, such as a string or cylinder, to impart a desired shape to the aggregates, such as a shape that is less densely packed than cellular aggregates without the structure, and which permits plasma to pass through the aggregates. The specific geometry and shape of the structure can also be designed to maintain the aggregated particles away from the filter, thereby more easily permitting the plasma to pass therethrough without clogging. These examples are not meant to be limiting, and any structure having the desired properties, provided it meets size and other requirements as would be understood by one skilled in the art, can be used as the starting particles for forming the cellular aggregates. In all embodiments described herein, the term "agglutinating agent" will refer to the use of an agglutinating agent alone, or in combination with a structure as described above, which has been coated with an agglutinating agent. Agglutinating agent 12 is housed in primary collection chamber 38 of primary tube 24 once tube 26 is evacuated and hermetically sealed. A secondary tube 124 is further provided including cylindrical tubular wall 128 extending between closed end 130 and open end 132 in a similar manner as with primary tube 24. Secondary tube 124 is evacuated and hermetically sealed at open end 132 with a conventional rubber stopper 142, similar to stopper 42. The secondary tube 124 can be any blood collection tube known in the art comprised of glass or plastic matrix. Interior surface 134 of secondary tube 124 hermetically sealed with rubber stopper 142 defines secondary collection chamber 138.

Device 10 further includes a transfer device 54 for transfer of plasma from primary tube 24 to secondary tube 124, as will be discussed in more detail herein. Transfer device 54 is comprised of tubular plastic cylinder 56 having hollow partition 62 internally therein, and desirably spaced equidistant from the opposing ends of cylinder 56. Cylinder 56 has exterior surface 58 and interior surface 60, with an internal diameter that is larger than the diameter of primary tube 24 and secondary tube 124. Partition 62 is comprised of upstream convex disk 64 and downstream convex disk 66, both desirably molded during manufacture to interior surface 34 of cylinder 56. The exterior surfaces of partition 62 and interior surface 60 of plastic cylinder 56 define upstream chamber 74 and downstream chamber 76 of transfer device 54. The interior surfaces of convex disks 64, 66 define space 70, which houses porous filter 72.

Porous filter 72 is a filter matrix including pores which are sufficiently large enough to draw plasma therethrough under a normal vacuum of a conventional evacuated blood collection tube, but sufficiently small and including a long filtration path so as to catch and retain blood cell aggregates. Desirably, porous filter 72 is comprised of a high-density polyester or polypropylene, sintered plastic, glass fibers or any other material capable of creating a porosity size of equal to or greater than 10 microns. Variations of the structural shape of the porous filter are contemplated within the preferred embodiments.

Upstream needle 78 and downstream needle 82 are mounted in upstream convex disk 64 and downstream convex disk 66 of hollow partition 62, respectively, and point in opposite directions relative to each other. Upstream needle 78 is positioned within upstream chamber 74 of transfer device 54 and downstream needle 82 is positioned within downstream chamber 76 of transfer device 54 and are centered within interior surface 60 of cylinder 56. Upstream needle 78 provides fluid communication through upstream convex disk 64 to porous filter 72, and downstream needle 82 provides fluid communication through downstream convex disk 66.

Elastomeric needle sheaths 86, 88 are provided to cover upstream needle 78 and downstream needle 82, respectively, as known in the art. Elastomeric needle sheaths 86, 88 are flexibly slidable along needles 78, 82. Elastomeric needle sheaths 86, 88 act as a valve, provide means for an airtight seal between both needles 78, 82 during insertion of either needle 78, 82 through rubber stoppers 42, 142 hermetically sealed to primary tube 24 and secondary tube 124, respectively.

It is preferred that the length of cylinder 56 provides a safety measure, whereby tip 80 of upstream needle 78 covered by needle sheath 86 is completely contained within upstream chamber 74 of transfer device 54 and tip 84 of downstream needle 82 covered by needle sheath 88 is completely contained within downstream chamber 76 of transfer device 54.

In use, primary tube 24 is used in a standard phlebotomy procedure to collect blood in primary collection chamber 38 through standard intravenous collection practices. The reduced pressure established through the evacuated primary collection chamber 38 decreases as the volume of blood in primary collection chamber 38 increases. Upon entry into primary collection chamber 38, the blood contacts agglutinating agent 12 deposited therein and anticoagulant 14 coated on interior surface 34 of tube 26. Anticoagulant 14 prevents the blood from forming a clot, and agglutinating agent 12 binds blood cells into aggregate particles, or binds and aggregates the blood cells on a structure coated with the agglutinating agent, thereby separating the suspended blood cells from the plasma of the collected blood sample.

After the blood sample is collected within primary tube 24, aggregate particle formation is allowed to occur through agglutinating agent 12 acting on the whole blood sample. This may be facilitated, for example, by shaking the tube to adequately mix the agglutinating agent with the whole blood sample. At any point after collection of the sample within primary tube 24, the downstream end of primary tube 24 is inserted into upstream chamber 74 of transfer device 54. As such, tip 80 of upstream needle 78 pierces through rubber stopper 42 and upstream needle 78 is inserted through rubber stopper 42 into primary collection chamber 38 of primary tube 24. Optionally, prior to inserting primary tube 24 into upstream chamber 74 of transfer device 54, a vent needle 16 may be inserted through rubber stopper 42. Vent needle 16 desirably includes a small gauge needle with an air permeable vent filter 18 attached on the end opposite needle tip 20. Vent needle 16 provides for venting of the pressure in primary collection chamber 38 by equilibrating the air pressure inside primary collection chamber 38 with atmospheric air pressure.

After primary tube 24 is inserted into upstream chamber 74 of transfer device 54, secondary tube 124 is inserted into downstream chamber 76 of transfer device 54. As such, tip 84 of downstream needle 82 pierces through rubber stopper 142 and downstream needle 82 is inserted through rubber stopper 142 into secondary collection chamber 138 of secondary tube 124. Rubber needle sheath 88 covering downstream needle 82 is pushed by top surface 144 of rubber stopper 142 of secondary tube 124, whereby an airtight seal exists between needle sheath 88 and top surface 144 of rubber stopper 142.

Once tip 84 of downstream needle 82 pierces through rubber stopper 142, the reduced pressure inside secondary collection chamber 124 creates a pressure differential or force that draws the agglutinated blood in primary collection chamber 38 through upstream needle 78 of transfer device 54 into porous filter 72. The agglutinated blood cells become trapped in porous filter 72, while allowing the plasma to pass through porous filter 72 into downstream needle 82 and into secondary collection chamber 138 of secondary tube 124. As the blood volume in primary collection chamber 38 decreases, vent needle 16, if optionally used, equilibrates the pressure inside primary collection chamber 38 with the atmospheric air pressure entering primary collection chamber 38 through vent needle 16. The atmospheric equilibrated air pressure inside primary collection chamber 38 facilitates the transfer of the plasma through porous filter 72 into secondary collection chamber 138 by the reduced pressure of secondary tube 124. The resulting plasma specimen inside secondary collection chamber 138 is contaminant-free and ready for subsequent transfer for diagnostic analysis.

FIGS. 4-13 depict further embodiments of the present invention, and include many components which are substantially identical to the components of FIGS. 1-3. Accordingly, similar components performing similar functions will be numbered identically to those components of FIGS. 1-3, except that a suffix "a" will be used to identify those similar components in FIGS. 4-6, a suffix "b" will be used to identify those similar components in FIGS. 7-9, and a suffix "c" will be used to identify those similar components in FIGS. 10-13.

Figure 4:
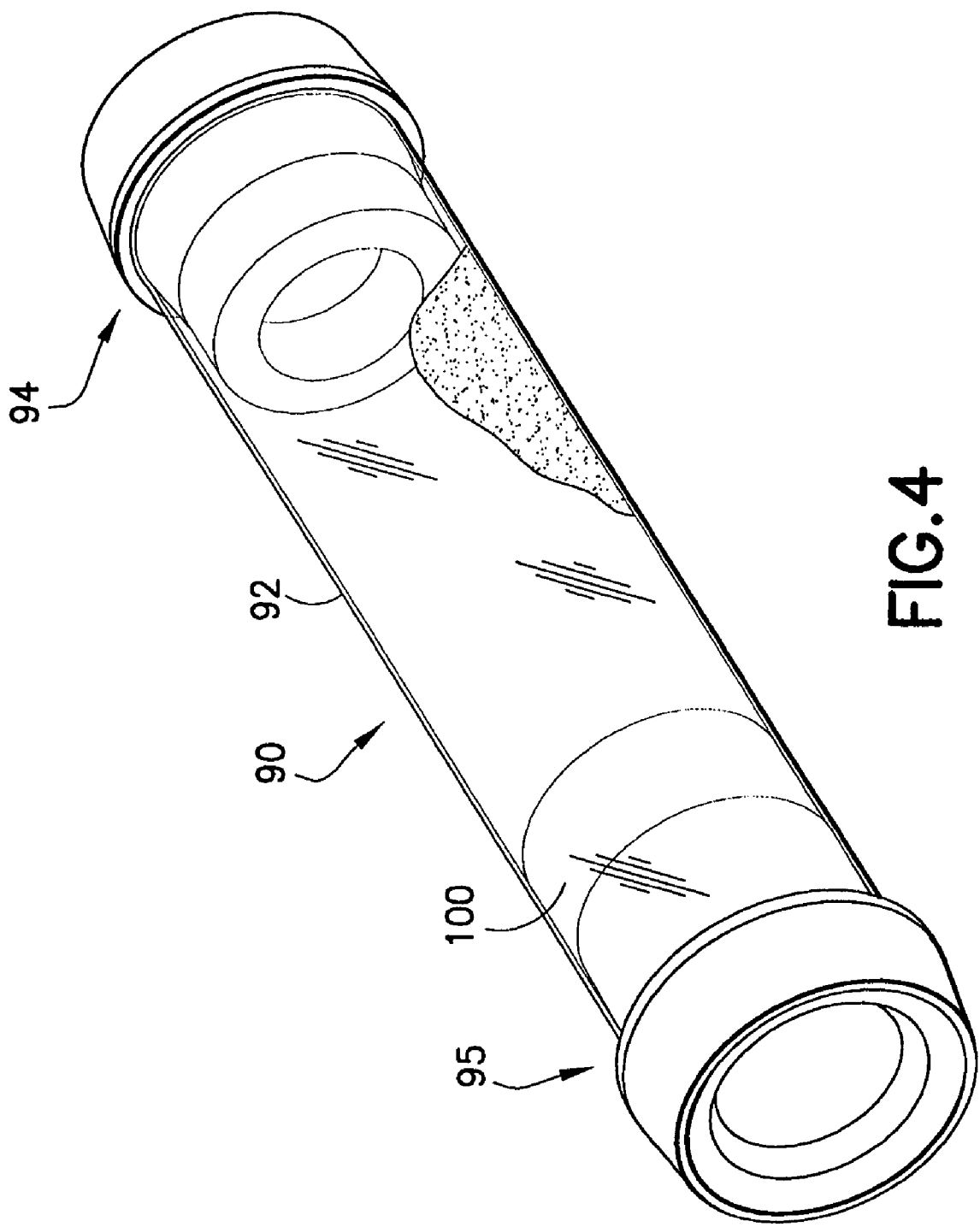
FIG. 4 is a perspective view of a second embodiment of a primary collection chamber made in accord with the present invention having a double-ended, evacuated primary tube with a filter disposed therein.
Figure 5:
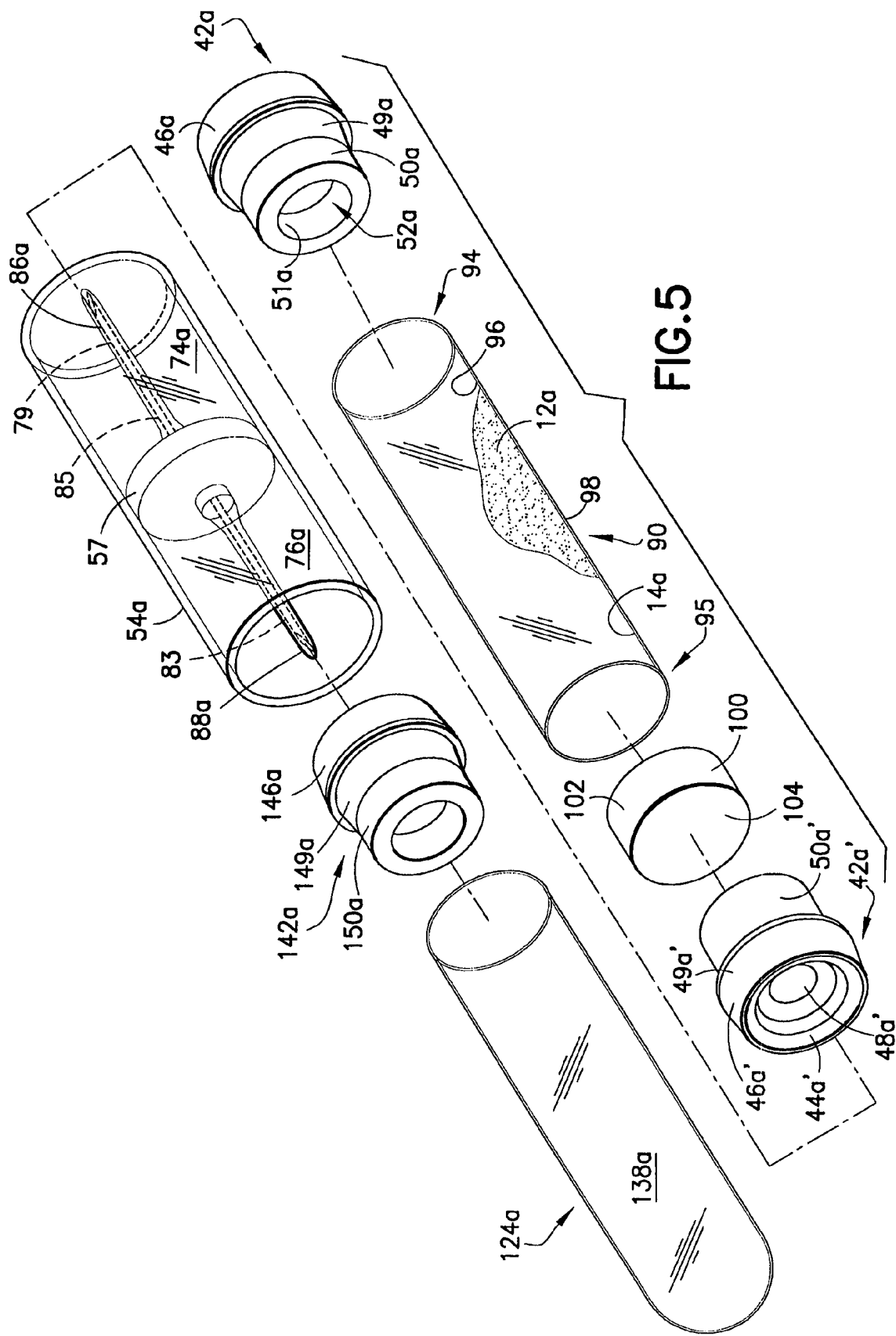
FIG. 5 is an exploded view of the device of FIG. 4 in use with a transfer device and secondary tube.
Figure 6:
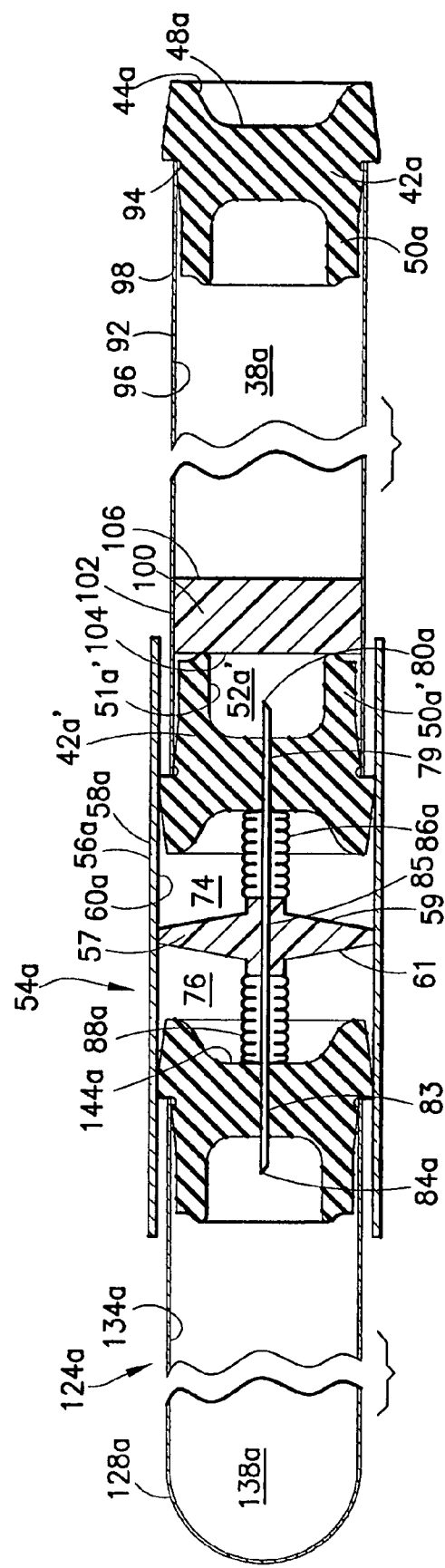
FIG. 6 is a sectional view of the device of FIG. 4 shown in use as in FIG. 5.

As shown in detail in FIGS. 4 through 6, in a second embodiment of the present invention, collection tube 90 comprises a hollow cylindrical tube including generally cylindrical tubular wall 92 extending between a first open end 94 and a second open end 95. First and second open ends 94 and 95 are hermetically-sealed with rubber stoppers 42a and 42a', respectively, such as rubber stopper 42 as previously described herein. Tubular wall 92 has interior surface 96 and exterior surface 98. Collection tube 90 is comprised of suitable material which is impermeable to gas and liquid, and is desirably made of glass or molded plastic. Optionally, vent needle 16a is provided for use with rubber stopper 42a of collection tube 90.

Similar to the previous first embodiment of primary tube 24, rubber stoppers 42a, 42a' are hermetically sealed at circumferential surface 49a, 49a' of depending portion 50a, 50a' to interior surface 96 at the first open upstream end 94 and the second open downstream end 95 of collection tube 90.

Cylindrical porous filter 100 is positioned within collection tube 90 and affixed along circumferential surface 102 of filter 100 to interior surface 96 of collection tube 90. Porous filter 100 is positioned so that downstream surface 104 of filter 100 abuts up against depending portion 50a' of downstream rubber stopper 42a'. Abutting porous filter 100 against downstream rubber stopper 42a' encloses cavity 52a' of depending portion 50a' of rubber stopper 42a'. The interior surface 96 of collection tube 90 between interior surface 51a of cavity 52a of depending portion 50a of upstream rubber stopper 42a and upstream surface 106 of porous filter 100 define primary collection chamber 38a of primary collection tube 90. Prior to evacuation of tube 90 and hermetically sealing the circumferential surfaces 49a, 49a' of depending portions 50a, 50a' of rubber stoppers 42a, 42a' to interior surface 96 of tube 90, anticoagulant 14a is coated on interior surface 96 of tube 92, and agglutinating agent 12a is deposited inside primary collection chamber 38a of primary tube 90.

The alternate embodiment of collection tube 90 shown in FIG. 4 is intended for use with a transfer device which is modified from transfer device 54 described above. In particular, as shown in FIGS. 5 and 6, transfer device 54a includes plastic cylinder 56a which includes a solid partition 57 positioned inside cylinder 56a equidistant from the opposing ends of cylinder 56a. Cylinder 56a has exterior surface 58a and interior surface 60a. Cylinder 56a has an interior diameter that is larger than the diameters of primary collection tube 90 and secondary tube 124a. Solid partition 57 is shaped as a solid bi-convex disk, which is molded to interior surface 60a along the circumferential surface of the partition during manufacture of cylinder 56a. Upstream surface 59 and downstream surface 61 of partition 57 and interior surface 60a of cylinder 56a define upstream chamber 74a and downstream chamber 76a of transfer device 54a, respectively.

Double-ended needle 85 is mounted in solid partition 57. Double-ended needle 85 has upstream portion 79 with upstream tip 80a and downstream portion 83 with downstream tip 84a. Double-ended needle 85 is mounted in partition 57 such that upstream portion 79 and downstream portion 83 are centrally located within transfer device 54a. Double-ended needle 85 provides fluid communication through solid partition 57.

Rubber needle sheaths 86a, 88a are provided to cover upstream tip 80a and downstream tip 84a, respectively, as described above.

In the method of use of the embodiment of FIGS. 4-6, blood is collected in primary collection chamber 38a of primary collection tube 90 through standard venous collection practices in a similar manner as described above. The reduced pressure within the evacuated primary collection chamber 38a decreases as the volume of blood in primary collection chamber 38a increases. Upon entry into primary collection chamber 38a, the blood is exposed to agglutinating agent 12a deposited therein and anticoagulant 14a coated on interior surface 34a of primary collection chamber 38a. Agglutinating agent 12a assisted by anticoagulant 14a creates aggregate particles, thereby separating the suspended blood cells from the plasma component of the blood sample.

After several minutes to allow aggregate particle formation, the downstream end of primary collection tube 90 is inserted into upstream chamber 74a of transfer device 54a, whereby upstream tip 80a of upstream portion 79 of double-ended needle 85 pierces through the downstream rubber stopper 42a' of primary collection tube 90 and upstream portion 83 of double-ended needle 85 inserts into cavity 52a' within depending portion 50a' between rubber stopper 42a' and filter 100. Optionally, prior to or during insertion of the downstream end of primary collection tube 90 into upstream chamber 74a of transfer device 54a, vent needle 16a may be inserted through upstream rubber stopper 42a of primary collection tube 90 to equilibrate the air pressure inside primary collection chamber 38a with atmospheric air pressure. While primary collection tube 90 is being inserted into transfer device 54a, rubber needle sheath 86a of upstream portion 79 of double-ended needle 85 is forced to slide along upstream portion 79 of needle 85 towards partition 57. The tip end of sheath 86a maintains contact with top surface 44a' of downstream rubber stopper 42a' creating a near airtight seal between rubber needle sheath 86a and top surface 44a' of rubber stopper 42a'.

Once upstream portion 79a of double-ended needle 85 is fully inserted, tip 80a of upstream portion 79 of double-ended needle 85 is positioned within cavity 52a' of depending portion 50a' of rubber stopper 42a' without becoming embedded in porous filter 100. Thereafter, the upstream end of a secondary tube 124a is inserted into downstream chamber 76a of transfer device 54a, whereby tip 84a of downstream portion 83 of double-ended needle 85 pierces through rubber stopper 142a of secondary tube 124a and downstream portion 83 of double-ended needle 85 is inserted into secondary collection chamber 138a. As downstream portion 83 of double-ended needle 85 is inserted through rubber stopper 142a of secondary tube 124a, rubber needle sheath 88a is forced by rubber stopper 142a to slide along downstream portion 83 of needle 85 towards partition 57, whereby a nearly airtight seal is formed between the tip of needle sheath 88a and top surface 144a of rubber stopper 142a of secondary tube 124a.

Once the tip of the downstream portion 83 of double-ended needle 85 pierces through rubber stopper 142a, the reduced pressure inside secondary collection chamber 138a creates a pressure differential that draws the agglutinated blood in primary collection chamber 38a towards and into the porous filter 100 within the primary collection tube 90. Porous filter 100 blocks passage of the aggregate particles but allows the plasma to pass through into double-ended needle 85, and then into secondary collection chamber 138a of secondary tube 124a. As the blood volume in primary collection chamber 38a decreases, vent needle 16a, if optionally used, equilibrates the pressure inside primary collection chamber 38a with atmospheric air. The resulting plasma specimen drawn into secondary collection chamber 138a is contaminant-free and ready for subsequent transfer for diagnostic analysis.

Figure 7:
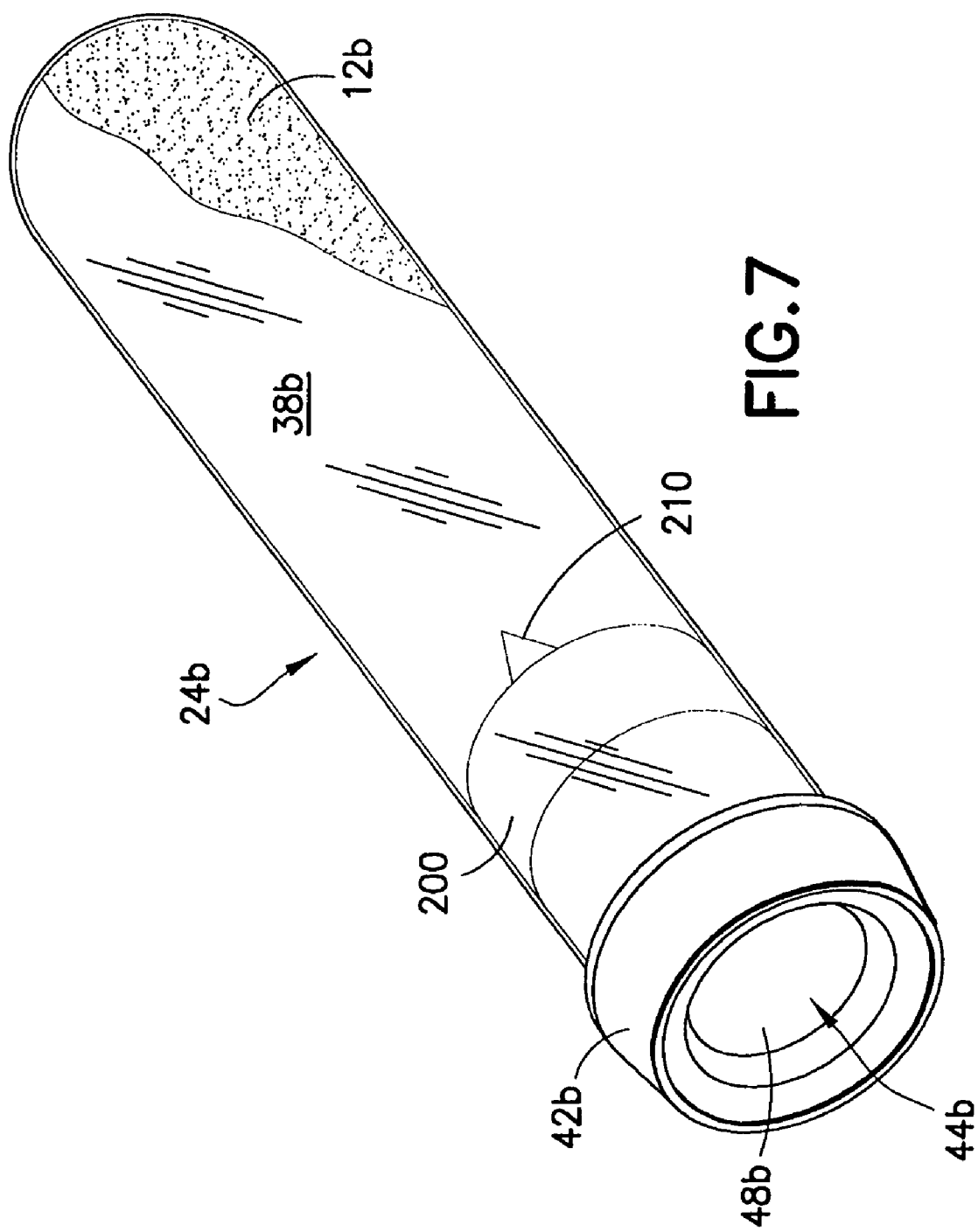
FIG. 7 is a perspective view of a third embodiment of a primary collection chamber made in accord with the present invention having an evacuated primary tube having a porous filter with a one-way valve therein.
Figure 8:
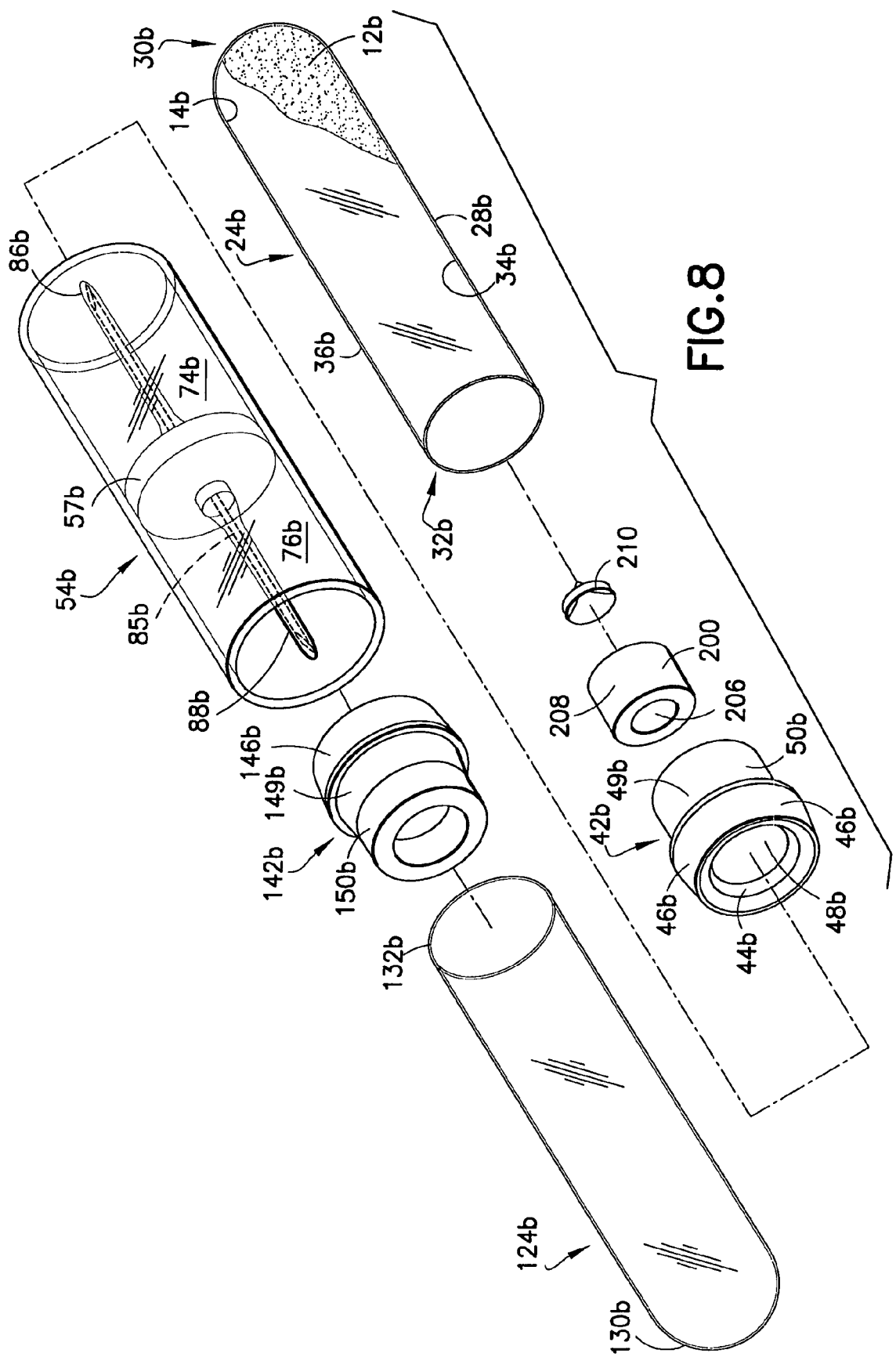
FIG. 8 is an exploded view of the device of FIG. 7 in use with a transfer device and secondary tube.
Figure 9:
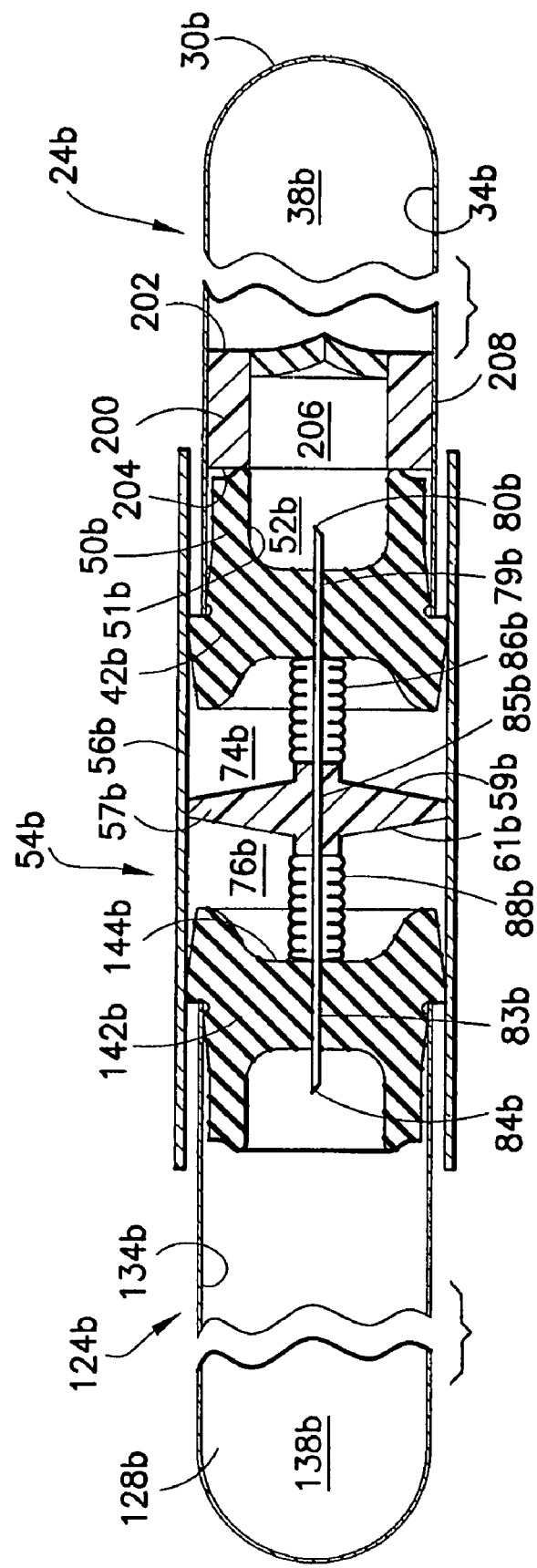
FIG. 9 is a sectional view of the device of FIG. 7 shown in use as in FIG. 8.
Figure 10:
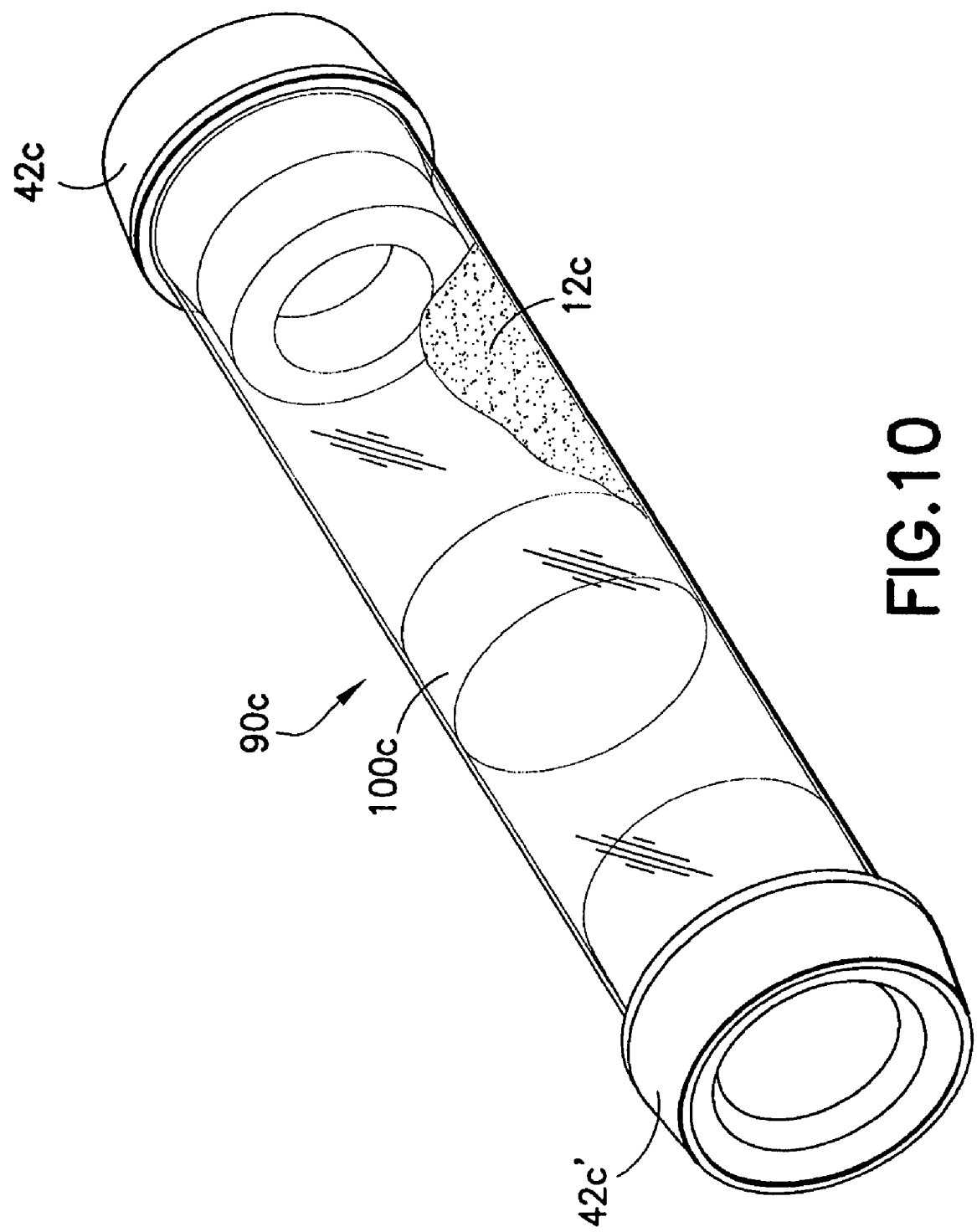
FIG. 10 is a perspective view of a fourth embodiment of a primary collection chamber made in accord with the present invention having a double-ended tube with a porous filter disposed therein.
Figure 11:
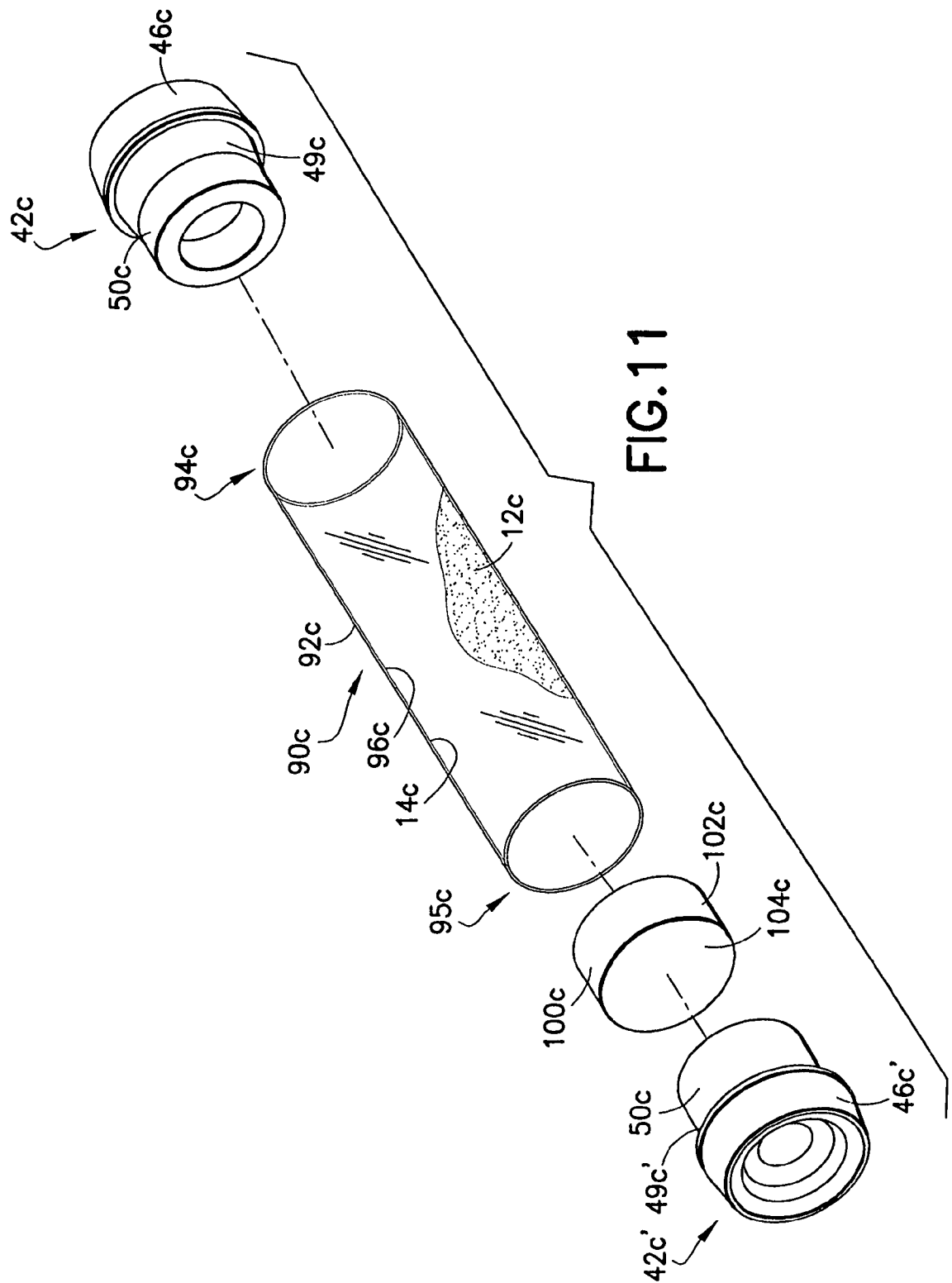
FIG. 11 is an exploded view of the device as shown in FIG. 10.
Figure 12:
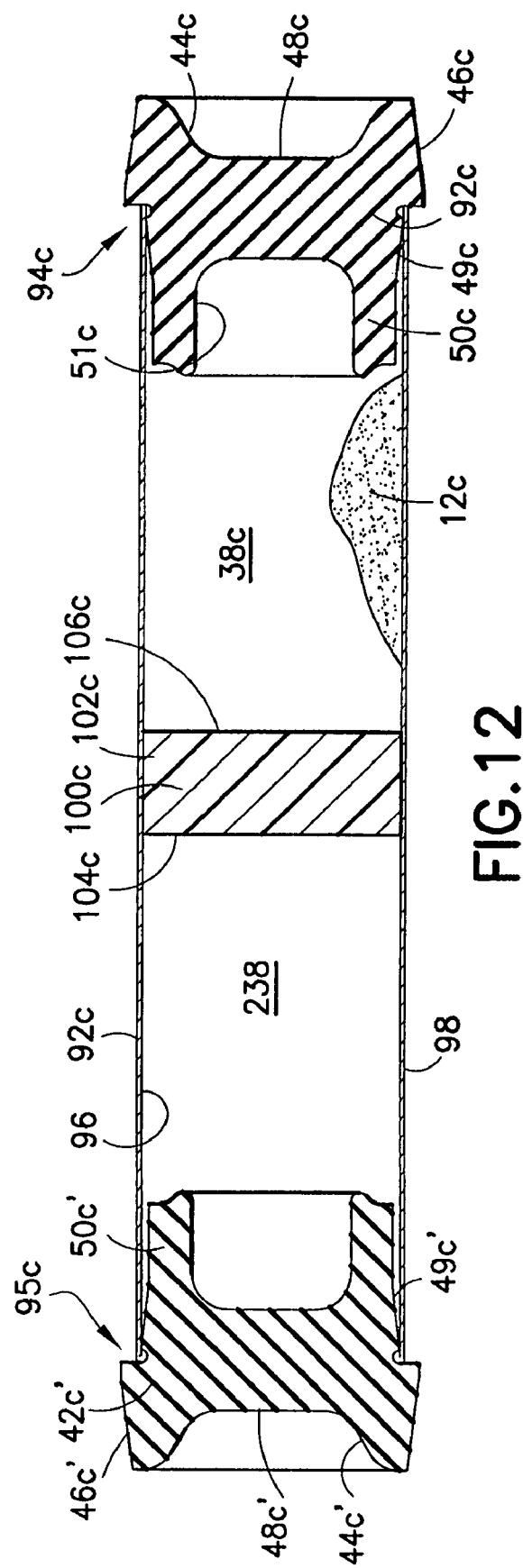
FIG. 12 is a sectional view of the device as shown in FIG. 10.

FIGS. 7 through 9 depict a further embodiment of the invention including primary tube 24b hermetically sealed with rubber stopper 42b. Tube 24b includes generally cylindrical tubular wall 28b extending between closed end 30b and open end 32b. Tube 24b has interior surface 34b and exterior surface 36b. Tube 24b is similar in construction to tube 24 described above, and may be comprised of a suitable material which is impermeable to gas and liquid, and is desirably made of glass or molded plastic.

Porous filter 200 is provided within tube 24b. Porous filter 200 is annular in shape, extending between upstream end 202 and downstream end 204, with central bore 206 extending through the length of filter 200. Outer circumferential surface 208 of porous filter 200 is affixed to interior surface 34b of primary tube 24b. A rubber one-way valve 210 is provided in sealed relation with upstream end 202 of porous filter 200 at the upstream opening of central bore 206. One-way valve 210 allows blood to flow in only one direction, through central bore 206 and into primary collection chamber 38b of primary tube 24b, while preventing back flow of blood into central bore 206 from primary collection chamber 38b of primary tube 24b. For example, one-way valve 210 may be a "duckbill" type valve, which permits flow of fluid in only one direction, or may be a self-sealing membrane which permits puncturing therethrough.

Rubber stopper 42b, as previously discussed herein, is provided having depending portion 50b, which is sealed along circumferential surface 49b to interior surface 34b of the downstream end of primary tube 24b. Downstream end 204 of porous filter 200 abuts against depending portion 50b of rubber stopper 42b, closing cavity 52b. Interior surface 34b of primary tube 24b and upstream end 202 of porous filter 200 having one-way valve 210 affixed thereto define primary collection chamber 38b of primary tube 24b.

Prior to affixing porous filter 200 to interior surface 34b of primary tube 24b, anticoagulant 14b is coated on interior surface 34b of the tube and agglutinating agent 12b is deposited inside the primary collection chamber 38b.

In the method of use of the embodiment of FIGS. 7-9, blood collection from a patient is accomplished by insertion of a blood collection needle during a standard procedure through rubber stopper 42b and into central bore 206. Blood can then be drawn into the space within central bore 206 and pass through one-way valve 210 and into primary collection chamber 38b based on the reduced pressure within primary collection chamber 38b. More desirably, the blood collection needle is inserted into and through one-way valve 210, such that blood can be collected from the patient and directly into primary collection chamber 38b based on the reduced pressure therein.

Upon entry into primary collection chamber 38b, the blood is exposed to anticoagulant 14b coated on interior surface 34b of primary collection chamber 38b and agglutinating agent 12b deposited therein. Blood cells bind to agglutinating agent 12b to form aggregate particles. One-way valve 210 maintains the blood sample in primary collection chamber 38b of primary tube 24b.

After the whole blood is sufficiently exposed to the agglutinating agent 12b allowing formation of aggregate particles, the downstream end of primary tube 24b is inserted into upstream chamber 74b of transfer device 54b, whereby tip 80b of upstream portion 79b of double-ended needle 85b pierces through rubber stopper 42b. Upstream tip 80b of needle 85b is only inserted until it reaches a position such that upstream tip 80b is positioned within central bore 206 of annular porous filter 200.

Then, the upstream end of a separate secondary tube 124b is inserted into downstream chamber 76b of transfer device 54b, whereby downstream tip 84b of downstream portion 83b of double-ended needle 85b pierces through rubber stopper 142b of secondary tube 124b and downstream portion 83b of needle 85b inserts into secondary collection chamber 138b. Once tip 84b of downstream portion 83b of needle 85b pierces through rubber stopper 142b, the reduced pressure inside secondary collection chamber 138b creates a force or pressure differential that draws the agglutinated blood from primary collection chamber 38b into porous filter 200, whereby the aggregate particles become stuck in filter 200. The plasma passes through the upstream face end 202 and into central bore 206 of filter 200, through double-ended needle 85b, and into secondary collection chamber 138b of secondary tube 124b. The resulting plasma specimen inside secondary collection chamber 124b is contaminant-free and ready for subsequent transfer for diagnostic analysis.

Yet a further embodiment is shown in detail in FIGS. 10 through 13. In this embodiment, collection tube 90c comprises an evacuated hollow cylindrical tube including generally cylindrical tubular wall 92c extending between a first open end 94c and a second open end 95c. First and second open ends 94c and 95c are hermetically sealed with rubber stoppers 42c and 42c', respectively, such as rubber stopper 42 as previously described herein. Tubular wall 92c has interior surface 96c and exterior surface 98c. Collection tube 90c is comprised of suitable material as described above. Rubber stoppers 42c, 42c' are hermetically sealed at circumferential surface 49c, 49c' of depending portion 50c, 50c' to interior surface 96c of the first open upstream end 94c and the second open downstream end 95c of collection tube 90c, as described above.

Cylindrical porous filter 100c is positioned within collection tube 90c and affixed along circumferential surface 102c of filter 100c to interior surface 96c of collection tube 90c. Porous filter 100c is positioned substantially centrally within collection tube 90c, desirably substantially equidistant between first and second open ends 94c and 95c. The interior space within collection tube 90c between upstream surface 106c of porous filter 100c and the interior surface 51c of cavity 52c of depending portion 50c of upstream rubber stopper 42c define primary collection chamber 38c of collection tube 90c. The interior space within collection tube 90c between downstream surface 104c of porous filter 100c and the interior surface 51c' of cavity 52c' of depending portion 50c' of downstream rubber stopper 42c' define an ancillary chamber or secondary collection chamber 238, also within collection tube 90c.

Anticoagulant 14c is coated on interior surface 96c of the portion of collection tube 90c upstream of porous filter 100c defining primary collection chamber 38c, and agglutinating agent 12c is deposited inside such space defining primary collection chamber 38c.

In the method of use of this embodiment, blood is collected in primary collection chamber 38c of evacuated collection tube 90c by standard intravenous collection practices through insertion of a standard blood collection needle through upstream rubber stopper 42c. Such whole blood is exposed to anticoagulant 14c and agglutinating agent 12c deposited therein. Upon entering primary collection chamber 38c, the blood cells begin to form aggregate particles. As the blood is drawn into primary collection chamber 38c and the volume of blood therein increases, the reduced pressure within primary collection chamber 38c decreases, that is, the pressure increases. The separation established within collection tube 90c through porous filter 100c permits the blood to congregate, with the aggregated blood cells collecting on the upstream surface 106c of porous filter 100c, forming a partial blocking of air. This in turn causes the negative pressure within secondary collection chamber 238 on the downstream side of porous filter 100c to be maintained, created a pressure gradient between primary collection chamber 38c and secondary collection chamber 238. As such, the reduced pressure within secondary collection chamber 238 creates a force that draws the blood sample into porous filter 100c, whereby the aggregate blood cells become trapped in filter 100c and the plasma is drawn through filter 100c into secondary collection chamber 238.

Figure 13:
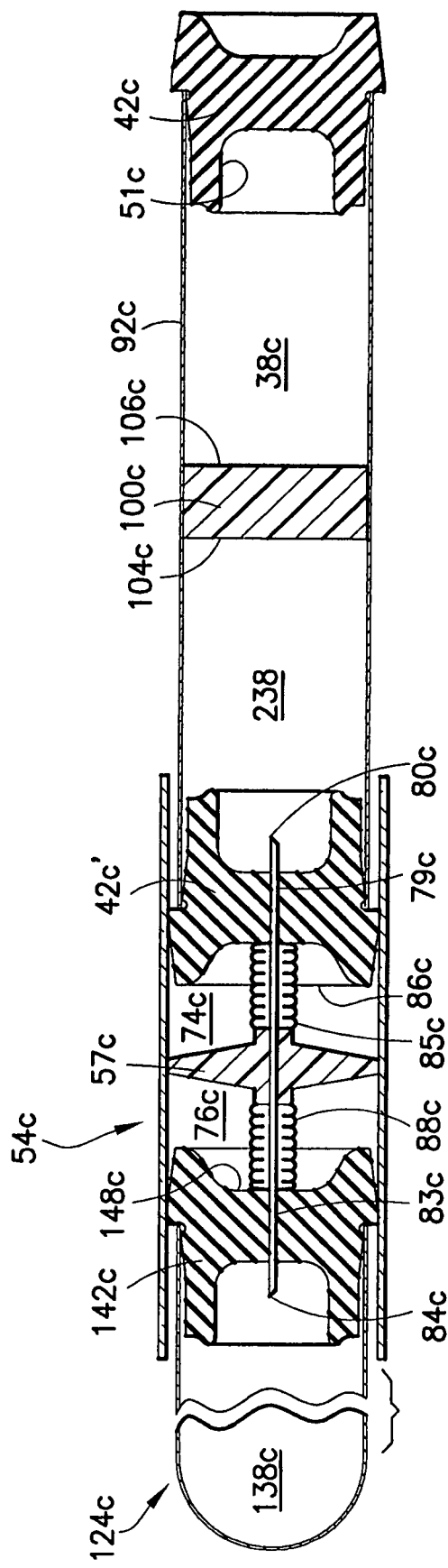
FIG. 13 is a sectional view of the device of FIG. 10 in use with a transfer device and an evacuated secondary tube.

To further facilitate the separation and to transfer the thus-separated plasma into a secondary container, a transfer device 54c may be used, as shown in FIG. 13. As such, the downstream end of collection tube 90c is inserted into an upstream chamber 74c of transfer device 54c, whereby upstream tip 80c of upstream portion 79c of needle 85c pierces through downstream rubber stopper 42c' and upstream portion 79c of needle 85c slides into the ancillary chamber provided through secondary chamber 238. A further evacuated container or tube such as tube 124c can then be inserted into downstream chamber 76c of transfer device 54c as described above. As such, the plasma within the ancillary chamber defined by secondary collection chamber 238 is then drawn through double-ended needle 85c into tube 124c, and is contaminant-free and ready for subsequent transfer for diagnostic analysis.

The present invention provides an effective and simple method for separating plasma from a whole blood sample without the risk of contamination through opening of the containers. Portions of the assembly of the present invention can be supplied together as a kit of parts, thereby facilitating the method of transfer embodied within the invention.

While the present invention is satisfied by embodiments in many different forms, there is shown in the drawings and described in detail herein the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed is:

1. A kit of parts for collecting a whole blood sample and for separating plasma from the whole blood sample, the kit comprising:
   an evacuated primary collection container comprising a pierceable closure at one end thereof, said primary collection container including a blood agglutinating agent therein for binding blood cells within a whole blood sample;
   an evacuated secondary collection container comprising a pierceable closure at one end thereof; and
   a transfer housing comprising a first needle member for piercing the pierceable closure of the primary collection container, a second needle member for piercing the pierceable closure of the secondary collection container, and a porous filter positioned between the first needle member and the second needle member such that fluid communication between the primary collection container and the secondary collection container is established through the porous filter,
   wherein the porous filter includes a pore size adapted to permit transfer of plasma therethrough while preventing the transfer of bound blood cells therethrough.

2. A kit as in claim 1, wherein the primary collection container further includes an anticoagulant therein.

3. A kit as in claim 1, wherein the transfer housing includes structure for supporting the primary collection container and the secondary collection container when the first needle member and the second needle member pierce the respective pierceable closures thereof.

4. A kit as in claim 1, further comprising a first pierceable sheath extending over the first needle member and a second pierceable sheath extending over the second needle member.

5. A kit as in claim 1, wherein a pressure differential established between the secondary collection container and the primary collection container permits transfer of plasma through said porous filter while preventing the transfer of bound blood cells therethrough.

6. A kit as in claim 5, further comprising an air vent adapted to establish a pressure equilibrium between the primary collection container and atmospheric pressure during transfer of plasma from the primary collection container to the secondary collection container.

7. A kit as in claim 6, wherein the vent comprises a needle member for piercing through the pierceable closure of the primary collection container.

8. A container as in claim 1, wherein the agglutinating agent comprises a structure coated with an agglutinating agent.

* * * * *